(12) United States Patent
James-Meyer et al.

(10) Patent No.: US 12,396,976 B2
(45) Date of Patent: *Aug. 26, 2025

(54) FORMULATIONS HAVING ANTI-INFLAMMATORY ACTIVITY AND ANTIMICROBIAL ACTIVITY AGAINST GRAM-POSITIVE BACTERIA

(71) Applicant: NATUREZA RESEARCH, INC., Denison, TX (US)

(72) Inventors: Lynn S. James-Meyer, Denison, TX (US); Gerald C. Coles, Bristol (GB)

(73) Assignee: Natureza Research, Inc., Denison, TX (US)

( * ) Notice: Subject to any disclaimer, the term of this patent is extended or adjusted under 35 U.S.C. 154(b) by 264 days.

This patent is subject to a terminal disclaimer.

(21) Appl. No.: 17/035,508

(22) Filed: Sep. 28, 2020

(65) Prior Publication Data

US 2021/0077449 A1    Mar. 18, 2021

Related U.S. Application Data

(63) Continuation of application No. 15/526,304, filed as application No. PCT/US2015/056111 on Oct. 16, 2015, now Pat. No. 10,786,477.

(60) Provisional application No. 62/064,574, filed on Oct. 16, 2014.

(51) Int. Cl.
*A61K 31/23* (2006.01)
*A61K 9/00* (2006.01)
(Continued)

(52) U.S. Cl.
CPC ............ *A61K 31/23* (2013.01); *A61K 9/0014* (2013.01); *A61K 9/127* (2013.01); *A61K 9/1271* (2013.01);
(Continued)

(58) Field of Classification Search
CPC ...... A61K 31/23; A61K 9/0014; A61K 9/127; A61K 9/1271; A61K 9/19; A61K 31/20;
(Continued)

(56) References Cited

U.S. PATENT DOCUMENTS

| | | |
|---|---|---|
| 6,204,230 B1 | 3/2001 | Taylor et al. |
| 7,846,895 B2 | 12/2010 | Eckert et al. |

(Continued)

FOREIGN PATENT DOCUMENTS

| | | |
|---|---|---|
| JP | 01197431 A | 9/1989 |
| WO | WO 2007/031519 | 3/2007 |

(Continued)

OTHER PUBLICATIONS

EP Communication and Supplementary European Search Report for EP 18843511.9, delivered/mailed Dec. 9, 2020, European Patent Office, Munich, Germany, (13 pages).

(Continued)

*Primary Examiner* — Bethany P Barham
*Assistant Examiner* — Alexandra Nicole Isnor

(57) ABSTRACT

Novel active compositions having antimicrobial and anti-inflammatory activity are described, the activity provided by an active component prepared in a suspension, the active component being at least a single chain fatty acid having a carbon length of 12, or between 12 and no more than 18. The fatty acid may be esterified and/or ethylated or methylated. As an antimicrobial the active component has activity against one or more microorganisms including *Staphylococcus* spp., *Streptococcus* spp., *Mycobacterium* spp., *Clostridium* spp., and *Candida* spp., with an MIC as low as 0.0018 µg/ml. As an anti-inflammatory, it is at least as or is more effective than cyclosporine in preventing T-cell proliferation in response to a trigger, such as stimulation by the one or more microorganisms. The active component is more (Continued)

active when combined with a phospholipid (e.g., lecithin, phosphatidylcholine) and caused to form liposomal nanoparticles. It is also more active when caused to form coated liposomal nanoparticles. Compositions with said active components may be provided internally and/or topically on a surface or on skin.

20 Claims, 1 Drawing Sheet

(51) Int. Cl.
  *A61K 9/127*   (2025.01)
  *A61K 9/1271*   (2025.01)
  *A61K 9/19*   (2006.01)
  *A61K 31/20*   (2006.01)
  *A61K 47/12*   (2006.01)
  *A61K 47/24*   (2006.01)
  *A61K 47/46*   (2006.01)
  *C07F 9/10*   (2006.01)

(52) U.S. Cl.
  CPC ............... *A61K 9/19* (2013.01); *A61K 31/20* (2013.01); *A61K 47/12* (2013.01); *A61K 47/24* (2013.01); *A61K 47/46* (2013.01); *C07F 9/103* (2013.01); *A61K 9/0095* (2013.01); *Y02A 50/30* (2018.01)

(58) Field of Classification Search
  CPC ........ A61K 47/12; A61K 47/24; A61K 47/46; A61K 9/0095; C07F 9/103; Y02A 50/30
  USPC ......................................................... 424/489
  See application file for complete search history.

(56) References Cited

U.S. PATENT DOCUMENTS

| | | |
|---|---|---|
| 2008/0262084 A1 | 10/2008 | Daftary et al. |
| 2011/0237686 A1 | 9/2011 | Ng et al. |
| 2012/0178731 A1 | 7/2012 | Guthery |
| 2013/0289005 A1 | 10/2013 | Guthery |
| 2014/0051650 A1 | 2/2014 | Ardolino et al. |
| 2015/0157591 A1 | 6/2015 | Zhu et al. |
| 2016/0175244 A1 | 6/2016 | Schlievert |
| 2016/0303148 A1 | 10/2016 | Kozono et al. |

FOREIGN PATENT DOCUMENTS

| | | |
|---|---|---|
| WO | WO 2008/062428 | 5/2008 |
| WO | WO 2008/137917 | 11/2008 |
| WO | WO 2016/061561 | 4/2016 |

OTHER PUBLICATIONS

Yang D., et al., The antimicrobial activity of liposomal lauric acids against *Propionibacterium acnes*, Biomaterials, Aug. 8, 2009 (online), vol. 30, pp. 6035-6040.

Notification of Transmittal of the International Search Report and the Written Opinion of the International Searching Authority, with the International Search Report and Written Opinion of the International Searching Authority, for International Application No. PCT/US2015/56111, mailed Jan. 7, 2016, 11 pages.

Notification Concerning Transmittal of International Preliminary Report on Patentability, with International Preliminary Report on Patentability, for International Application No. PCT/US2015/56111, mailed Apr. 27, 2017, 8 pages.

Kato S., et al., Effect of pH on the antimicrobial action of sucrose laurate, Food Hygiene and Safety Science, Jun. 1986, vol. 27, issue 3, pp. 218-223.

Zhang X., et al., Comparative study of surface-active properties and antimicrobial activities of disaccharide monsters, PLoS ONE, Dec. 22, 2014, 9(12):e114845, DOI:10.1371/journal.pone.0114845, pp. 1-19.

Kabara, et al., Fatty acids and derivatives as antimicrobial agents, Antimicrobial Agents Chemother., 1972, vol. 2(1), pp. 23-28.

Hattori, et al., Effects of long-chain fatty acids and fatty alcohols on the growth of *Streptococcus mutans*, Chem. Pharm. Bull., 1987, vol. 35(8), pp. 3507-3510.

Sun, et al., Antibacterial actions of fatty acids and monoglycerides against Helicobacter pylori, FEMS Immunology Medical Microbiol., 2003, vol. 36, pp. 9-17.

EPO Form 1507S, EPO Communication for extended European Search Report, for EP Application No. 15850205.4, mailed Mar. 28, 2018 (1 page).

Supplementary European Search Report and Annex to the European Search Report and Information on Search Strategy, and Examination via EPO Form 1703, for EP Application No. 15850205.4, mailed Mar. 28, 2018 (6 pages).

Zhang, H., et al., "Quantitative structure-activity relationships of antimicrobial fatty acids and derivatives against *Staphylococcus aureus*," J. Zhejiang Univ-Sci B (Biomed & Biotechnol) 2012 vol. 13(2):83-93.

Notification Concerning Transmittal of International Preliminary Report on Patentability, for International Application No. PCT/US2018/046576, mailed Feb. 20, 2020, 1 pg.

PCT International Preliminary Report on Patentability, for International Application No. PCT/US2018/046576, mailed Feb. 20, 2020, 7 pgs.

"Lecithin" descriptions, Science Direct, available at https://www.sciencedirect.com/topics/chemistry/lecithin, downloaded Feb. 24, 2020.

Kabara, J., et al., Relationship of chemical structure and antimicrobial activity of alkyl amides and amines, Antimicrob Agents and Chemother 1972 vol. 2(6):492-498.

Shapiro, S., The inhibitory action of fatty acids on oral bacteria, Oral Microbiol Immunol 1996 vol. 5:350-355.

Abstract, JP 01-197431 A, Sunamoto et al., published Aug. 9, 1989, 2 pgs.

Supplementary European Search Report and Annex to the European Search Report and Information on Search Strategy, and Examination via EPO Form 1703 and EPO Form 1507S, for EP Application No. 15850205.4, mailed Mar. 28, 2018 (7 pages).

Zhang, H., et al., Quantitative structure-activity relationships of antimicrobial fatty acids and derivatives against *Staphylococcus aureus*, J Zhejiang Unv-Sci B (Biomed & Biotechnol 2012 vol. 13(2):83-93.

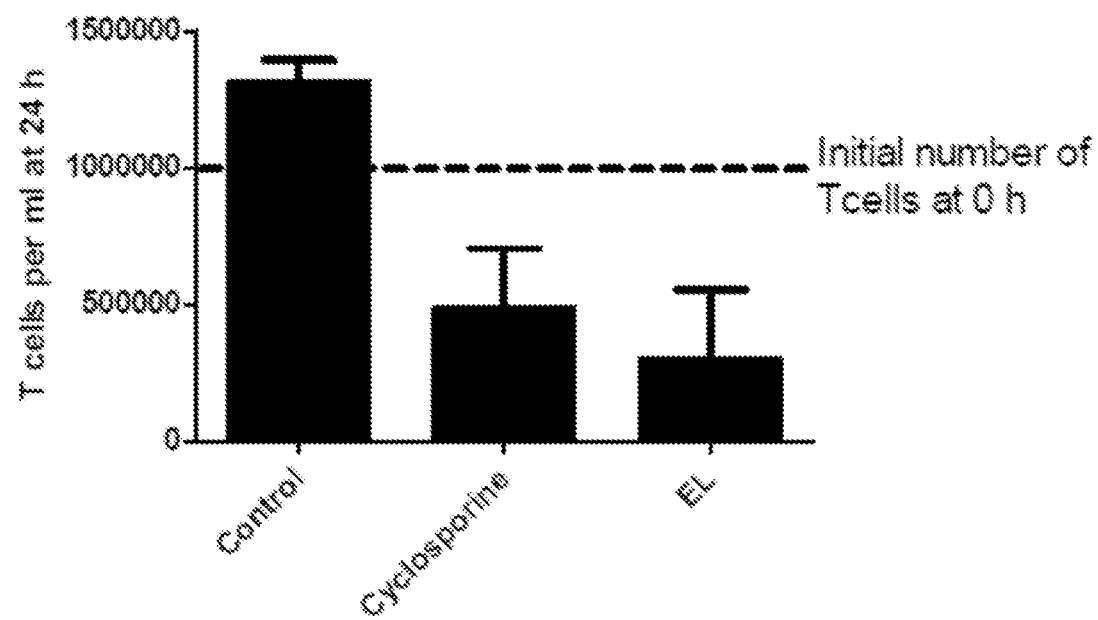

FORMULATIONS HAVING ANTI-INFLAMMATORY ACTIVITY AND ANTIMICROBIAL ACTIVITY AGAINST GRAM-POSITIVE BACTERIA

CROSS REFERENCE TO RELATED APPLICATIONS

This application is a continuation from U.S. patent application Ser. No. 15/526,304, which claims the benefit of International Application No. PCT/US2015/056111 with an International filing date of Oct. 16, 2015, which claims the benefit of U.S. Provisional Application No. 62/064,574 filed Oct. 16, 2014, the entirety of each being incorporated herein by reference

BACKGROUND

Some of the most common bacterial infections stem from Gram positive bacteria, including *Staphylococcus* spp., *Streptococcus* spp., *Clostridium* spp., and *Mycobacterium* spp. *Staphylococcus* infections are found on the skin, upper respiratory regions, gastro-intestinal tract and urogenital tract. *Staphylococcus* infections account for at least half of all hospital acquired infections for bacteremia. *Streptococcus* infections are some of the most common, and, in addition to strep throat, lead to diseases such as pneumonia, sinusitis, otitis, meningitis, endocarditis, toxic shock syndrome, necrotizing fasciitis, rheumatic fever, scarlet fever, pharyngitis, glomerulonephritis, and wound infections, to name a few. *Clostridium* is an anaerobic, endospore forming bacteria found ubiquitously in the soil, water, sewage and gastro-intestinal tract. It also produces a toxin with effects generally irreversible. *Mycobacterium* is the cause of TB and leprosy. TB is now a pandemic and is the primary killer of persons with HIV in Africa.

The most common cause of fungal infections is from various species of *Candida*. Persons with diabetes or impaired immune responses are more susceptible to infections from *Candida*. Overgrowth is often caused by antibacterial treatment, and the overgrowth of certain species is associated with thrush, and vaginal and gastro-intestinal infections.

The ineffectiveness of many current therapies for the treatment of the described bacteria and yeast remains a large concern as the world's population grows and continues to cross borders. For example, the resistance of *Staphylococcus* bacteria to many current antibiotic therapies is pronounced, and includes resistance to penicillin, methicillin, and vancomycin. Antibiotic overuse or prolonged use is also associated with increased infections with *Candida*. There remains a need to provide selective and targeted therapies for these pervasive and infectious agents. In addition, there remains a need for therapies that are safer and are more effective than many current antibiotic treatments as continued use and overuse of current antibiotics has led to various multi-drug resistant bacterial species as well *Candida* overgrowth and increases in *Candida* infections. With findings that bacterial and fungal resistance to antibiotics occurs in as short a period of time as 18 months and possibly less than 18 months, there remains a need for therapies that overcome such antibiotic resistance patterns.

OVERVIEW

Described herein are new and improved compositions and new uses of said new compositions as described below, said compositions useful and utilized for inhibiting growth of certain microorganisms, for killing certain microorganisms, and as antimicrobial formulations having activity and effectiveness, or preferred activity and preferred effectiveness, against certain or select microorganisms and bacteria, including select gram positive bacteria. In one or more embodiments, the select microorganisms include microorganisms and gram positive bacteria excluding microorganisms and bacteria residing in a digestive system of an animal/mammal (e.g., excluding "beneficial" microbiota or gastrointestinal flora, such as *Lactobacillus acidophilus*, *Bifidobacterium bifidum*, *E. coli*). In one or more embodiments, the select microorganisms include microorganisms and gram positive bacteria excluding microorganisms and bacteria residing on the skin of an animal/mammal (e.g., excluding "skin flora" or skin microbes or skin microbiota considered beneficial). In one or more embodiments, the select microorganisms include microorganisms and gram positive bacteria excluding microorganisms and bacteria residing in the oral cavity of an animal/mammal (e.g., excluding oral microbes or oral microbiota considered beneficial). In one or more embodiments, the select microorganisms may include some beneficial microbiota while also or more selectively targeting microorganisms and bacteria in an amount and/or in a type considered harmful to said animal/mammal.

In one or more forms are improved active compositions that include an active component comprising at least a medium chain fatty acid. Preferably, the medium chain fatty acid is a so-called "linear" chain saturated fatty acid or a monocarboxylic acid. The active component may be a fatty acid ester having at least 12 carbon atoms in a linear chain (C-12) or from 12 to 18 carbon atoms in a linear chain (C-12 to C-18), in a total amount up to about 50 wt. % of the composition, or between about 0.001 and 50 wt. %. The active component may be selected from at least one of an ethyl and/or a methyl fatty acid ester having at least the 12 carbon chain (C-12), or fatty acid esters from 12 to 18 carbon chains, in a total amount up to about 50 wt. % of the composition, or between about 0.001 and 50 wt. %. The fatty acid may be dodecanoate. In some embodiments, the active component may comprise a fatty acid ester selected from any of an ethyl or methyl fatty acid ester of 12 carbon atoms, in a total amount up to about 50 wt. % of the composition, or between about 0.001 and 50 wt. %. The fatty acid may be an esterified ethyl dodecanoate or an esterified methyl dodecanoate. The active component will generally be provided for use in pharmaceutical grade purity, having been specifically extracted and/or fractionated and modified to the esterified form, including the esterified ethyl or esterified methyl form. The purity of the active component, such as but not limited to the esterified ethyl dodecanoate or the esterified methyl dodecanoate, may be provided having a purity greater than 95%, or greater than 99%. The active component may be provided with a solvent. The solvent may be an organic compound in solution. The solvent may be water. In one or more embodiments, a first active antimicrobial composition as described herein may include or may consist essentially of the active component (as described herein) and the solvent (as described herein). The activity of the first active composition being provided by the active component (as described herein) and the solvent (as described herein). The activity of the first active composition includes antimicrobial activity (e.g., having activity against susceptible microorganisms and/or having a lower MIC against the susceptible microorganisms than expected or previously found, and capable of being provided at a suitable dose for antimicrobial activity and/or effectiveness as an antimicrobial). The activity of the first active composition includes anti-inflammatory activity (e.g., preventing T cell proliferation in response to a trigger or anti-inflammatory response, and/or preventing T-cell proliferation in response to stimulation by a microorganism, and capable of being provided at a suitable dose for anti-inflammatory activity and/or effectiveness as an anti-inflammatory agent). Said first active composition may be further provided in any form suitable to internalize the first active composition and/or to topically apply the first active composition. In one or more embodiments, providing the first active composition in any form suitable to internalize the composition and/or to topically apply the first active composition will not minimize and/or will not substantially affect activity of an active portion of the active composition. In one or more embodiments, an active portion of the first active antimicrobial composition may be, or may include, or may consist essentially of the active component (as described herein) and the solvent (as described herein).

The active component may further include at least one phospholipid. In some embodiments, the phospholipid is a neutral phospholipid. In some embodiments, the phospholipid may be charged. The phospholipid is preferably but not limited to phosphatidylcholine (PC), lecithin, lecithin components (naturally occurring components) or by products (phosphatidylethanolamine (PE), phosphatidylinositol (PI), phosphatidic acid (PA), phosphatidylserine (PS), and lyso-phospholipids (e.g., lyso-phosphatidylethanolamine (LPE), sphyingomyelin (SPM)), and/or bulky fatty acids, such as cholesterol, or lipids having a chain length predominantly from about C-14 to C-20. The phospholipid is preferably in an amount between about 0.001 and 50 wt. % of the composition. In some embodiments, the phospholipid is predominantly phosphatidylcholine with an additional lipid, in a lesser amount, such as the lecithin or cholesterol, or a lipid having a chain length predominantly from about C-14 to C-20, or the additional lipid may be provided as bile or bile salts. Bile and/or bile salts may be included in the absence of any lecithin. Bile or bile salts may be provided as a replacement for lecithin. In some embodiments, the phospholipid is predominantly lecithin with an additional lipid, in a lesser amount, such as phosphatidylcholine or cholesterol, or a lipid having a chain length predominantly from about C-14 to C-20, or the bile or bile salts. In some embodiments, the phospholipid is or is substantially phosphatidylcholine. In some embodiments, the phospholipid is or is substantially lecithin. The lecithin may be from any source. The lecithin may be from a natural source, such as egg lecithin, soy lecithin. The phospholipid will act in part as a carrier. In one or more embodiments, a second active composition as described herein may include or may consist essentially of the active component (as described herein) and the phospholipid (as described herein). The activity of the second active composition being provided by the active component (as described herein) and the phospholipid (as described herein). The activity of the second active composition may be greater than activity of the first active composition (e.g., the second active composition having a lower MIC against susceptible microorganisms and/or having a larger anti-inflammatory effect, thereby capable of being provided at a lower dose for a same or similar activity and/or effectiveness). Said second active antimicrobial composition may be further provided in any form suitable to internalize the second active composition and/or to topically apply the second active composition. In one or more embodiments, providing the second active composition in any form suitable to internalize the second active composition and/or to topically apply the second active composition will not minimize and/or will not substantially affect activity of an active portion of the second active composition. In one or more embodiments, an active portion of the second active composition may be, or may include, or may consist essentially of the active component (as described herein) and the phospholipid (as described herein).

In one or more embodiments, a third active composition as described herein may include or may consist essentially of the active component (as described herein), the solvent (as described herein) and the phospholipid (as described herein). The activity of the third active composition being provided by the active component (as described herein), the solvent (as described herein) and the phospholipid (as described herein). The activity of the third active composition may be greater than activity of the first active composition (e.g., the third active composition having a lower MIC against susceptible microorganisms and/or having a larger anti-inflammatory effect, thereby capable of being provided at a lower dose for a same or similar activity and/or effectiveness). The activity of the third active composition may be greater than activity of the second active antimicrobial composition (e.g., the third active composition having a lower MIC against susceptible microorganisms and/or having a larger anti-inflammatory effect, thereby capable of being provided at a lower dose for a same or similar activity and/or effectiveness). Said third active composition may be further provided in any form suitable to internalize the third active composition and/or to topically apply the third active composition. In one or more embodiments, providing the third active composition in any form suitable to internalize the third active composition and/or to topically apply the third active composition will not minimize and/or will not substantially affect activity of an active portion of the third active composition. In one or more embodiments, an active portion of the third active composition may be, or may include, or may consist essentially of the active component (as described herein), the solvent (as described herein) and the phospholipid (as described herein).

In some embodiments, the active component when combined with at least the phospholipid may further include a coating. The coating may be linear polysaccharides. The coating may be antibodies. The coating may be a functionalized coating, such as one or more functionalized polymers. The coating may be a protein, such as albumin. The coating may include a combination of antibodies and/or linear polysaccharides and/or functionalized polymers and/or proteins. In one or more embodiments, a fourth active composition as described herein may include or may consist essentially of the active component (as described herein), the phospholipid (as described herein) and the coating as described herein). The activity of the fourth active composition being provided by the active component (as described herein), the phospholipid (as described herein), and the coating (as described herein). The activity of the fourth active composition may be greater than activity of the first active composition (e.g., the fourth active composition having a lower MIC against susceptible microorganisms and/or having a larger anti-inflammatory effect, thereby capable of being provided at a lower dose for a same or similar activity and/or effectiveness). The activity of the fourth active composition may be greater than activity of the second active antimicrobial composition (e.g., the fourth active composition having a lower MIC against susceptible microorganisms and/or having a larger anti-inflammatory effect, thereby capable of being provided at a lower dose for a same or similar activity and/or effectiveness). The activity of the fourth active composition may be greater than activity of the third active antimicrobial composition (e.g., the fourth active composition having a lower MIC against susceptible microorganisms and/or having a larger anti-inflammatory effect, thereby capable of being provided at a lower dose for a same or similar activity and/or effectiveness). Said fourth active composition may be further provided in any form suitable to internalize the fourth active composition and/or to topically apply the fourth active composition. In one or more embodiments, providing the fourth active composition in any form suitable to internalize the fourth active composition and/or to topically apply the fourth active composition will not minimize and/or will not substantially affect activity of an active portion of the fourth active composition. In one or more embodiments, an active portion of the fourth active composition may be, or may include, or may consist essentially of the active component (as described herein), the phospholipid (as described herein), and the coating (as described herein).

In one or more embodiments, a fifth active composition as described herein may include or may consist essentially of the active component (as described herein), the solvent (as described herein), the phospholipid (as described herein) and the coating as described herein). The activity of the fifth active composition being provided by the active component (as described herein), the solvent (as described herein), the phospholipid (as described herein), and the coating (as described herein). The activity of the fifth active composition may be greater than activity of the first active composition (e.g., the fifth active composition having a lower MIC against susceptible microorganisms and/or having a larger anti-inflammatory effect, thereby capable of being provided at a lower dose for a same or similar activity and/or effectiveness). The activity of the fifth active composition may be greater than activity of the second active composition (e.g., the fifth active composition having a lower MIC against susceptible microorganisms and/or having a larger anti-inflammatory effect, thereby capable of being provided at a lower dose for a same or similar activity and/or effectiveness). The activity of the fifth active composition may be greater than activity of the third active composition (e.g., the fifth active composition having a lower MIC against susceptible microorganisms and/or having a larger anti-inflammatory effect, thereby capable of being provided at a lower dose for a same or similar activity and/or effectiveness). Said fifth active composition may be further provided in any form suitable to internalize the fifth active composition and/or to topically apply the fifth active composition. In one or more embodiments, providing the fifth active composition in any form suitable to internalize the fifth active composition and/or to topically apply the fifth active composition will not minimize and/or will not substantially affect activity of an active portion of the fifth active composition. In one or more embodiments, an active portion of the fifth active composition may be, or may include, or may consist essentially of the active component (as described herein), the solvent (as described herein), the phospholipid (as described herein), and the coating (as described herein).

Any of the active compositions when formulated may be in suspension. Any of the active compositions when formulated may be in a dry form, such as a powder or a particulate or a crystallized form. Any of the active compositions when formulated may be in a gel. Any of the active compositions when formulated may be in an emulsion. Any of the active compositions may be lyophilized or dried. Any of the active compositions are suitable for storing. Any of the active compositions when formulated may be stable at ambient or room temperature. The active compositions may be miscible in water. The active compositions are not soluble in water. In one or more embodiments, the active compositions when formulated may be in an optically clear suspension. In one or more embodiments, the active compositions may be in the form of or caused to form liposomes or micelles.

Any of the active compositions described herein may function, have activity, and/or be effective internally, when introduced internally, and may be introduced internally to a subject in need thereof. Internally, the active composition will have activity and/or be effective against selective internal microorganisms, including internal microorganisms and Gram-positive bacteria considered unsuitable or non-beneficial. Internally, the active composition will have activity and or be effective in at least preventing T-cell proliferation. Any of the active composition may operate, have activity, and/or be effective on a surface or skin, when introduced on the surface or on the skin, and may be introduced topically to a surface or to a subject in need thereof. Topically, on the surface or skin, the active composition will have activity and/or be effective against selective topical microorganisms, including surface microorganisms, skin microorganisms, and Gram positive bacteria and yeast. The Gram-positive bacteria may include or be exclusive to those considered unsuitable or non-beneficial. Topically, on the surface or on skin, the active composition will have activity and or be effective in at least preventing T-cell proliferation. Unlike disinfectant formulations, the active compositions described herein do not require another surfactant for activity. Unlike disinfectant formulations, the active compositions described herein, in one or more embodiments, do not require a nonmetabolizable surfactant, one that is not totally metabolized when ingested for activity. Unlike disinfectant formulations, the active compositions described herein do not require a polyol, such as a glycol or glycerol, for activity. When the active component described herein is combined with a glycol or glycerol, specific activity of the active component may become reduced. The subject may include a human or an animal.

Unlike disinfectant formulations (which have non-selective antimicrobial activity and little if any anti-inflammatory activity), the active compositions described herein exhibit selective or a preferred activity against microorganisms considered to be in an amount or in a type unsuitable (e.g., harmful, not beneficial) for an animal or a human or a surface. The active compositions may operate, have activity, and/or be effective internally, when introduced internally, and may be introduced internally to a subject in need thereof. Internally, the active composition will have activity, preferred activity, and/or be effective or most effective against selective internal microorganisms, including Gram-positive bacteria or yeast considered unsuitable or non-beneficial. Internally, the active composition will have activity, preferred activity, and/or be effective or most effective in preventing T-cell proliferation in response to stimulation by the internal microorganism. The active compositions may operate, have activity, and/or be effective when introduced topically on the surface or on the skin, and may be introduced topically to the surface or to the skin of a subject in need thereof. Topically, the active composition will have activity a preferred activity, and/or be effective or most effective against selective topical, skin or surface microorganisms, including Gram-positive bacteria or yeast considered unsuitable or non-beneficial. Topically, the active composition will have activity, preferred activity, and/or be effective or most effective in preventing T-cell proliferation in response to stimulation by the internal microorganism.

The described active compositions prevent growth of at least *Staphylococcus* spp., *Streptococcus* spp., *Mycobacterium* spp., *Clostridium* spp., and types of *Candida*. The described active compositions prevent T-cell proliferation in response to stimulation by at least said microorganisms. The active compositions described herein do not prevent growth or are less effective against beneficial Gram positive bacteria of the gastro-intestinal or genitourinary tract or oral cavity, as examples. No activity was seen against certain beneficial bacteria, such as *Lactobacillus acidophilus* and *Bifidobacterium bifidum*. The active compositions described herein do not prevent growth of or are much less effective against Gram negative bacteria, such as *Escherichia coli*. Said active compositions when provided as described herein are considered non-toxic to mammals and to the environment.

The described active component for active compositions described herein may also be in a salt form. The active component may also be in the form of an acid. The active component may also be in the form of an amide. The fatty acid or fatty acid ester is preferably a so-called linear, single chain (trans) saturated fatty acid or its isomer (cis). In some embodiments, the fatty acid is or may include a fatty acid that has at least 12 carbon atoms (e.g., a laurate). Preferably, the C-12 fatty acid is saturated. In some embodiments, the fatty acid is a fatty acid that has at least 12 carbon atoms and may also be any of a C-13 to C-18 linear, single chain fatty acid, selected from but not limited to any of a myristate (C-14), palmitate (C-16), stearate (C-18), and combinations thereof. Preferably, the additional fatty acids (C-13 to C-18) are saturated. The fatty acid is found more active when esterified. The fatty acid is found more active when methylated (a fatty acid methyl ester). The fatty acid is found more active when ethylated (a fatty acid ethyl ester). The active component may be simply the fatty acid ester alone. The fatty acid or active component is often preferably the fatty acid ethyl ester alone, or often preferably the fatty acid ethyl ester alone, or may be a combination thereof. The active components described herein differ from alternative fatty acid compositions that are not selective as to the fatty acid chain length, and/or their purity, and/or their form, and/or include shorter chains, such 8 carbon atoms (C-8) or less and considered to be disinfectants, with poor broad-spectrum and no selective antimicrobial action.

Methods for preparing said active compositions are also described. The methods include combining at least said active component with any one or more of the solvent, the phospholipid, the coating, and suitable combinations thereof. The method further comprises mixing the combination. In some embodiments, the method includes forming a suspension containing at least the active component. In some embodiments, the method may further comprise undergoing evaporation, such as to remove at least some of the solvent. The method may further comprise causing the formation of a pro-drug. The method may further comprise causing the formation of liposome or micelle nanoparticles, in which the active component is retained in the liposomes or micelles and/or within an oil portion of the suspension. The method may further comprise filtering. The method may further comprise a coating step. The coating step includes providing a coating. The method may further comprise formulating and/or further processing for internal and/or topical use. The coating step and/or the further processing step may delay release of the active component. The coating step and/or the further processing step may target release and/or activity of the active composition.

The described compositions overcome an ongoing challenge to deliver a longer straight chain fatty acid ester, such as those that are C-12 and greater. This is because the longer the side chain, the less soluble said fatty acids are. Fatty acids that are C-12 and greater are insoluble and not deliverable internally. On the other hand, compositions described herein that include said fatty acid esters (or fatty acids or fatty acid amides or fatty acid salts) that are at least C-12 (or C-12 and greater) are deliverable internally. The described compositions are also selectively effective against Gram positive bacteria as well as *Candida* spp. Activity is seen against Gram positive, but not Gram negative bacteria. The compositions described herein overcome an ongoing desire to provide a composition that may be provided in a targeted manner and contain selectivity towards certain Gram positive bacteria without being directed toward beneficial Gram negative bacteria. As such, compositions described herein may be used in combination with agents that promote activity or encourage growth of Gram negative bacteria, especially ones that are useful in the gastro-intestinal tract, and genitourinary tract.

The active compositions described herein provide new active formulations for the treatment of susceptible infections from one or more microorganisms, including at least *Staphylococcus* spp. (internal and external, including wound infections, skin infections, and acne), *Streptococcus* spp. (internal and external, including wound infections, skin infections and tooth decay), *Clostridium* spp. (including infections with *C. difficile*), *Mycobacterium* spp. (including infections from TB, and Johne's disease) as well as *Candida* (including thrush, oral infections and vaginal infections). Said susceptible infections may also include respiratory tract infections, systemic infections, blood infections, gastrointestinal infections, urinary tract infections, skin infections, and genitourinary tract infections. The active compositions described herein provide new active formulations for the treatment of inflammation, or to reduce inflammation, or to reduce T-cell proliferation, such as inflammation triggered by the one or more microorganisms.

The active compositions described herein may be administered orally, topically, and/or internally. For internal administration, the compositions may be provided in a parenteral (IV, subcutaneous, intrasternal) form, including an intramuscular (IM) formulation, or provided in a form for inhalation. Effective excipients are included to facilitate certain administrations or forms of administration. Effective excipients may be included to enhance absorption.

In some embodiments, any of the new improved formulations may be administered in combination with another composition, such as a probiotic.

In some embodiments, the active compositions described herein may be combined with another antibacterial or anti-inflammatory agent, and/or with another antiviral agent, or with another antifungal agent, or with another anti-parasitic agent, or with another anti-infective agent. Said compositions alone or in combination may be used to provide a broad-spectrum effect with much higher efficacy and/or selective activity as compared with other broad-spectrum agents that do not have the higher efficacy and/or selective activity described herein.

In the description below, compositions with antibacterial activity and anti-inflammatory activity are described herein. At least some of the compositions include at least an active component comprising esterified fatty acids selected from at least one of an ethyl dodecanoate and a methyl dodecanoate in a total amount up to about 50 wt. % of the composition. At least some of the compositions also include at least an organic compound. At least some of the compositions also include at least phospholipid in an amount between about 0.5 and 20 wt. % of the composition. Any of said composition may be in a suspension, the suspension comprising liposomes containing the phospholipid and the active component. The phospholipid may be lecithin. The phospholipid may include lecithin. The phospholipid may be phosphatidylcholine. The composition may further comprise cholesterol in a non-esterified form. The composition may comprise no further or additional free fatty acids having a carbon chain length from 6 to 12, excluding the active component. The ethyl dodecanoate and the methyl dodecanoate may have pharmaceutical grade purity. The active component may further comprise a linear chain fatty acid selected from at least one of a fatty acid having a carbon chain length only from between 13 to 18. The antibacterial and anti-inflammatory activities may be provided by an active portion of the composition consisting essentially of the active component and the phospholipid. The antibacterial and anti-inflammatory activities may be provided by an active portion of the composition consisting essentially of the active component, the phospholipid, and the organic compound having fewer than 4 linear carbons. The composition may be lyophilized. The composition is suitable for storing. The composition is stable at ambient or room temperature. The composition is not soluble in water. The composition when in suspension may be an optically clear suspension. The liposomes may include a coating comprising linear polysaccharides. The coating may be chitosan. The liposomes may include a coating comprising antibodies. The antibacterial and anti-inflammatory activities may be provided by an active portion of the composition consisting essentially of the active component, the phospholipid, the coating, and optionally the organic compound, the organic compound having fewer than 3 linear carbons. The composition may be combined with bile. The composition inhibits growth of at least one of the group comprising *Staphylococcus* spp., *Streptococcus* spp., *Mycobacterium* spp., and *Clostridium* spp. and *Candida*. In some embodiments, the composition exhibits anti-inflammatory activity when the active component is in an amount at about an MIC for a susceptible microorganism or greater than the amount at about the MIC for the susceptible microorganism. In some embodiments, the composition exhibits anti-inflammatory activity when an amount of the active component is less than an amount at about an MIC of a susceptible microorganism. In some embodiments, the composition exhibits antimicrobial activity when the active component is in an amount at about an MIC for a susceptible microorganism or greater than the amount at about the MIC for the susceptible microorganism. In some embodiments, the composition exhibits anti-inflammatory activity when an amount of the active component is less than an amount at about an MIC of a susceptible microorganism. The composition is selectively active against certain susceptible Gram-positive bacteria without targeting beneficial Gram-positive bacteria when the active component is provided in an amount at an MIC for the certain susceptible Gram-positive bacteria or in an amount that is greater than the amount at the MIC for the certain susceptible Gram-positive bacteria. The composition is selectively active against certain susceptible Gram-positive bacteria without targeting Gram-positive negative bacteria when the active component is provided in an amount at an MIC for the certain susceptible Gram-positive bacteria or in an amount that is greater than the amount at the MIC for the certain susceptible Gram-positive bacteria In the description below, methods for preparing any of the active compositions having antimicrobial activity and anti-inflammatory activity are described. The methods may include combining at least an active component, an organic compound, and a phospholipid, the active component comprising esterified fatty acids selected from at least one of an ethyl dodecanoate and a methyl dodecanoate in a total amount up to about 50 wt. % of the composition, the phospholipid in an amount between about 0.5 and 20 wt. % of the composition, the organic compound having fewer than 3 linear carbons. The method further includes suspending and causing to form liposomes, the liposomes containing at least the active component and the phospholipid. The method may further comprise obtaining liposomal nanoparticles. The method may further comprise filtering to obtain liposomal nanoparticles. The combining may further comprises including cholesterol in an amount between about 0.04 and 6 wt. % of the composition. In the method, the phospholipid may be lecithin. In the method, the phospholipid may be phosphatidylcholine. In the method, the organic compound may be a weak acid or a buffered weak acid. In the method, the organic compound may be in a solution and pH of the solution is mildly acidic or between about pH 4 and about pH 6. The step of combining may include combining the active component in a solvent. The step of combining may include combining the active component with the phospholipid and the organic compound. The step of combining may include initially combining the phospholipid and the organic compound. The method may further comprise coating the liposomes with a coating comprising linear polysaccharides. The method may further comprise coating the liposomes with a coating comprising antibodies. The method may further comprise lyophilizing the liposomal nanoparticles. The method may further comprise providing the liposomal nanoparticles in a formulation for internal administration to a subject in need thereof to inhibit growth of infectious non-beneficial Gram positive bacteria. The method may further comprise providing the liposomal nanoparticles in a formulation for topical administration to a subject in need thereof to inhibit growth of infectious non-beneficial Gram positive bacteria. These and other embodiments are described below.

BRIEF DESCRIPTION OF THE DRAWINGS

For a more complete understanding of the description provided herein and the advantages thereof, reference is now made to the brief description below, taken in connection with the accompanying drawings and detailed description.

FIG. 1 depicts representative anti-inflammatory data as described herein with the representative active composition as described herein.

DETAILED DESCRIPTION

Although making and using various embodiments are discussed in detail below, it should be appreciated that as described herein are provided many inventive concepts that may be embodied in a wide variety of contexts. Embodiments discussed herein are merely representative and do not limit the scope of the invention.

Lauric acid, a 12-carbon (C-12) fatty acid or an example of a medium chain fatty acid, is generally insoluble and is difficult to prepare in a homogenous and stable suspension. While lauric acid has been found to exhibit some antimicrobial activity for external applications, it behaves, externally as a broad-spectrum anti-microbial (i.e., disinfectant)

with some or only modest potency against a wide variety of microbes, including viruses, bacteria (Gram positive and Gram negative), fungi as well as yeast. Internally, lauric acid will be converted to monolaurin (glycerol monolaurate), which is a surfactant, and is associate with mild and non-specific antimicrobial activity. Esterified lauric acid is laurate, which is also insoluble and even more difficult to suspend and to administer, especially internally. It is not currently known how to administer laurate internally (in the esterified form). Laurate has been shown to stimulate inflammatory activity in vitro and in macrophages and to activate inflammatory genes in cells.

It is also found that in general and with regard to their general and non-specific anti-microbial activity, medium chain fatty acids (e.g., C-6 to C-12) and long chain fatty acids (e.g., C-13-C-21) that exhibit any antibacterial activity are far less potent for external applications or when studied in vitro as compared with short chain fatty acids (e.g., fewer than six carbons). When anti-microbial activity is found in long chain fatty acids (in unsaturated forms) it is for external application and the activity is non-specific, therefore showing some inhibition of both Gram negative and Gram positive bacteria.

For lauric acid, as an example (a medium chain fatty acid), its potency has also been found to be quite significantly reduced when esterified and ethylated or methylated. In fact, while methyl laurate has, in some instances, shown some modest antibacterial activity in vitro, although significantly less potent than lauric acid, ethyl laurate is generally considered inactive with little or no antimicrobial activity (having been found to be than forty times less active).

Described herein are novel active compositions and methods of preparing said novel compositions that actually exhibit antimicrobial and anti-inflammatory activity. The antimicrobial activity is more active or potent than has been previously found or considered possible with the medium chain (e.g., C-12) and/or long chain (C-13 to C-18) fatty acids, in which the medium chain and/or long chain fatty acid provided in the manner described herein has become the predominant or principal active component, and, sometimes, the only active component of the novel active compositions described herein. Methods of preparing said novel active compositions described herein require specific features of said medium chain (e.g., C-12) and/or long chain (C-13 to C-18) fatty acids, said specific features found to provide the unexpected activity disclosed herein. In some embodiments, the novel active compositions described herein exhibit selective and/or preferred activity against Gram positive bacteria without activity or only very minimal or negligible activity against Gram negative bacteria. In some embodiments, the novel active compositions described herein exhibit selective or preferred activity against certain Gram positive bacteria. The novel active compositions described herein also exhibit activity against yeast or Candida spp. The selective activity or preferred activity may include activity against microorganism that are not considered beneficial microorganisms or are not generally considered to be microorganisms in amounts and/or types that are considered part of the normal or ordinary microbial flora or microbiota, which is a collection of microorganisms residing in an environment, such as the skin, oral mucosa, gastrointestinal tract, as examples. These microorganisms include bacteria and fungi (e.g., yeast). The selective activity or preferred activity may include selective or preferred activity against microorganism that are not considered beneficial microorganisms or are not generally considered to be microorganisms in amounts and/or types that are considered part of the normal or ordinary microbial flora or microbiota, while exhibiting less activity or minimal activity or negligible activity against microorganism that are considered beneficial microorganisms or are generally considered to be microorganisms in amounts and/or types that are considered part of the normal or ordinary microbial flora or microbiota.

The described active component or active agent in one or more of the active compositions described herein comprise at least a medium chain fatty acid, and optionally one or more long chain fatty acids. In some embodiments, the described active component or agent in compositions described herein comprise at least one of a medium chain fatty acid having a 12 carbon chain length and/or one or more of a long chain fatty acid having a chain length of 13 to 18 carbons. In some embodiments, the described active component or agent in active compositions described herein comprise at least one of a medium chain fatty acid ester having a 12 carbon chain length and/or one or more of a long chain fatty acid or long chain fatty acid ester having a chain length of 13 to 18 carbons. The ester form of the fatty acids described herein have been found to provide unexpectedly a higher potency than previously described and when provided in the compositions described herein. The ester form of the fatty acids described herein have been found to provide unexpectedly a selective activity (e.g., exhibiting greater activity against certain Gram positive bacteria), as has not been previously found, and when provided in the compositions described herein; non-targeted microorganisms included *Lactobacillus* and *Bifidobacterium*. The ester form of the fatty acids described herein have been found to provide unexpectedly no activity against Gram negative bacteria, not been previously found, and when provided in the compositions described herein. The ester form of the fatty acids described herein have been found unexpectedly to not target or have activity against Gram negative bacteria, not been previously found, and when provided in the compositions described herein. In some embodiments, potency can be manipulated with the compositions described herein. For example, less potency is observed when the fatty acid is in the form of a salt, or an acid. Reduced potency is observed with additional of glycol or glycerol. When in the form of an amide, the fatty acid amide may also have activity; however, in some embodiments, the activity may be reduced and/or less targeted or less selective (e.g., exhibiting activity against both Gram positive and Gram negative bacteria).

In one or more embodiments, the fatty acid is a fatty acid ester. In one or more embodiments, the fatty acid ester is an ethyl fatty acid ester or a methyl fatty acid ester. The fatty acids are often provided as free fatty acids. As an active component, said fatty acid or fatty acid ester may, therefore, be methylated, as a methylated fatty acid or fatty acid methyl ester, or may be ethylated, as an ethylated fatty acid or fatty acid ethyl ester. In some embodiments, the active component includes combinations of one or more of a methylated fatty acid, a fatty acid methyl ester, an ethylated fatty acid and/or a fatty acid ethyl ester. Thus, in one or more forms, the active component may be an esterified and/or methylated and/or ethylated straight chain saturated fatty acid or its isomer. In one or more forms, the active component may be an esterified and/or methylated and/or ethylated straight chain unsaturated fatty acid or its isomer. In some embodiments, at least one of the fatty acids has a chain length of 12 carbons. In some embodiments, the fatty acid is an ethyl laurate. In some embodiments, the fatty acid is a methyl laurate. In some embodiments, the fatty acid is an esterified ethyl laurate. In some embodiments, the fatty acid is an esterified methyl laurate. In one or more embodiments, combinations of the fatty acids described herein are provided as the active component.

In some embodiments, the fatty acid or active component or agent may be any one or more of a C-12 to a C-18 single chain free fatty acid, including but not limited to any of a laurate (C-12), myristate (C-14), palmitate (C-16), and stearate (C-18), and in various combinations thereof. In some embodiments, the fatty acid or active component may be a laurate (C-12), also referred to herein as a dodecanoate. In some embodiments, the fatty acid active component may be any one or more of a C-12 to a C-14 fatty acid, including but not limited to any of a laurate (C-12), and myristate (C-14), and combinations thereof. In some embodiments, the fatty acid or active component may be any one or more of a C-12 to a C-16 fatty acid, including but not limited to any of a laurate (C-12), myristate (C-14), and palmitate (C-16), and in various combinations thereof.

In some of the described compositions, the active portion or active formulation may include the active component or agent, in which the active component is at least or will include a saturated fatty acid (free fatty acid) selected from at least one of one of an ethyl and a methyl dodecanoate (a laurate or a linear 12 carbon chain fatty acid). The ethyl and/or methyl dodecanoate (12 carbon chain fatty acid) may be esterified. In some embodiments, the ethylated and/or methylated 12 carbon chain fatty acid is esterified. Additionally or alternatively, the ethylated and/or methylated 12 carbon chain fatty acid may be in a salt form, as an acid, or as an amide. The active component may comprise, in a total amount of the composition, up to about 50 wt. % of the composition. The wt. % may be based on a total volume. The active formulation may include or may also include as an active component an esterified saturated fatty acid selected from one or more of an ethyl and/or a methyl tetradecanoate (a myristate or a 14 carbon chain fatty acid), in which the active component, in total, is in a total amount of up to about 50 wt. % of the composition (based on a volume of the composition). The active formulation may include or may also include as an active component an esterified saturated fatty acid selected from one or more of an ethyl and/or a methyl hexadecanoate (a palmitate or a 16 carbon chain fatty acid), in which the active component, in total, is up to about 50 wt. % of the composition. The active formulation may include or may also include as an active component an esterified saturated fatty acid selected from one or more of an ethyl and/or a methyl octadecanoate (a stearate or an 18 carbon chain fatty acid), in which the active component, in total, is in amount of up to about 50 wt. % of the composition. Accordingly, in these embodiments, ethyl and/or methyl forms of any of the one or more active components, alone or in combination, may be used as the active component. Combinations of any of said fatty acid chain lengths may be used as the active component. In some embodiments, the active component is at least an ethyl dodecanoate or an ethyl laurate or a 12 carbon chain fatty acid or a methyl dodecanoate or a methyl laurate or an ethylated 12 carbon chain fatty acid or a methylated 12-carbon chain fatty acid. The active component in any of the formulations described herein may be at or about or up to about 50% wt/vol. as a final amount. In some embodiments, the active component in any of the formulations described herein may be at or about or up to about 20% wt/vol. as a final amount, or may be at or about or up to about 15% wt/vol., or may be at or about or up to about 10% wt/vol., or may be at or about or up to about 9% wt/vol., or may be at or about or up to about 8% wt/vol., or may be at or about or up to about 7% wt/vol., or may be at or about or up to about 6% wt/vol., or may be at or about or up to about 5% wt/vol. In one or more embodiments, and/or in use, the active component may also unexpectedly be in a final concentration of at or about or up to about 4% wt/vol., or may be at or about or up to about 3% wt/vol., may be at or about or up to about 2% wt/vol., or may be at or about or up to about 1.5% wt/vol., may be at or about or up to about 1% wt/vol., or may be at or about or as low as about 0.5% wt/vol., or may be at or about or as low as about 0.3% wt/vol., or may be at or about or as low as about 0.2% wt/vol., or may be at or about or as low as about 0.16% wt/vol., or may be at or about or as low as about 0.1% wt/vol., or may be at or about or as low as about 0.08% wt/vol., or may be at or about or as low as about 0.05% wt/vol., or may be at or about or as low as about 0.01% wt/vol., or may be at or about or as low as about 0.005% wt/vol., or may be at or about or as low as about 0.0025% wt/vol., or may be at or about or as low as about 0.002% wt/vol., or may be at or about or as low as about 0.0018% wt/vol. as a final concentration.

The fatty acid itself may be obtained from a natural source, such as an oil, including but not limited to a seed oil, including, for example, coconut oil, palm kernel oil, babassu oil, laurel oil, or may be a plant oil, or may be from milk (e.g., cow milk, goat milk, human breast milk, etc.). Unlike other compositions, however, the fatty acids described herein as the active component have been specifically extracted and/or fractionated to derive only the fatty acid(s) described herein. Moreover, fatty acids described herein as the active component have been specifically processed to the specified forms described herein (e.g., ester, amide, acid, ethylated, methylated, esterified and ethylated, esterified and methylated). For example, when including one of the preferred fatty acids, the ethyl dodecanoate or the methyl dodecanoate or the esterified ethyl dodecanoate or the esterified methyl dodecanoate, said fatty acid, when in any of the active compositions described herein, is generally provided in a medical grade or pharmaceutical grade purity, having been specifically processed (e.g., extracted, fractionated, modified, and purified) in a manner unique to the compositions described herein. In some embodiments, when a mixture of fatty acids as disclosed herein are included in an active composition, the mixture will include individually processed fatty acids, each being provided in a medical grade or pharmaceutical grade purity, having been specifically processed in the manner unique to the compositions described herein. In some embodiments, when a mixture of fatty acids as disclosed herein are included in an active composition, the mixture will be obtained only from a source having fatty acids as disclosed herein (e.g., C-12, or C-12 to C-18), and which has been processed to provide a medical grade or pharmaceutical grade purity, and in the manner unique to the compositions described herein (e.g., the mixture having a major or predominant C-12 fatty acid fraction with or without additional fatty acids from C-13 to -18 in a minor fraction and essentially minimal or no other chain lengths in the mixture, said fatty acids all having been suitably modified as described herein (e.g., esterified, ethylated, methylated, esterified and ethylated, and/or esterified and methylated)).

The fatty acid described herein, such as the ethylated or methylated fatty acid or ethylated or methylated fatty acid ester, may be provided and in a pure or substantially pure form and are not soluble. In some embodiments, the fatty acid is in a substantially pure or a pure form, to the extent that the pure form or the substantially pure form is available. Purity is often about or greater than about 90%, or about or greater than about 95%, or about or greater than about 97%, or about or greater than about 98%, or about or greater than about 99%. Purity may be at least about 95% or greater. The active component having said purity may be included in any of the active composition formulations without initial dilution or suspension. In some embodiment, purity may be greater than 50%, or greater than 60%, or greater than 70%, or greater than 80%.

The active component as described herein (e.g., the fatty acid(s) or the fatty acid ester(s)) are dispersible in water. The active component having said purity may be included in the formulation without initial dilution or suspension. The active component may be initially suspended and/or diluted in a solvent, in which the solvent is water or is an organic compound in solution, such as an alcohol or chloroform, or a weak acid. In some embodiments, the solvent is water. In some embodiments, the solvent is a weak acid. In some embodiments, the solvent is a buffered weak acid. The alcohol as a solvent may have some volatility. The organic compound as the solvent should also have some volatility. In some embodiments, the organic compound as described herein is a compound having fewer than 6 linear carbons. In some embodiments, the organic compound as described herein is a compound having fewer than 4 linear carbons. In some embodiments, the organic compound as described herein is a compound having 2 linear carbons. Alcohols of the organic compound include a primary alcohol (e.g., ethanol, methanol), a secondary alcohol (e.g., isopropanol), a tertiary alcohol or aliphatic alcohol. In some embodiments, the organic compound is one having a chemical formula R—COOH, or a carboxylic acid, in which R generally includes 4 or less linear carbons, or 3 or less linear carbons, or 2 or less linear carbons. The organic compound may be considered a volatile fatty acid or short chain fatty acid, and is not considered a medium chain fatty acid (e.g., 6 to 12 linear carbons). The organic compound may be one or a combination of the alcohol and/or carboxylic acid, and combinations thereof. The organic compound as a carboxylic acid may often be a weak acid (e.g., organic acid, such as formic acid, acetic acid, trichloroacetic acid, hydrofluoric acid, hydrocyanic acid, water, or a conjugate acid of a weak base), or may be a combination of the weak acid (COOH) and the salt form (containing the anion, COO—). For example, the organic compound may be predominantly a carboxylic acid, or may be predominantly a simple (short chain) carboxylic acid (e.g., acetic acid), or said carboxylic acid with some amount as a smaller amount or a minor amount of a buffer to keep the pH relatively constant, such as in the mildly acidic range (e.g., pH 4-6). Thus, in one or more embodiments, the solvent or buffer (e.g., a solution or suspension comprising the active component) may be mildly acidic, with a pH less than 7. In one or more embodiments, said solvent or buffer or suspension is mildly acid, having a pH about or less than about pH 6. In one or more embodiments, said solvent or buffer is mildly acid, having a pH between about 4 and about 6. A buffer for a weak acid may be a stable anion or salt form of the weak acid (e.g., sodium acetate). In some embodiments, the organic compound or alcohol is not a glycol or glycerol (polyol). Unexpectedly, and in contrast to what has been disclosed by others regarding use of these fatty acids described herein, the addition of glycol or glycerol has been found to reduce activity of the active component significantly. Without being bound by theory, the glycol or glycerol is believed to create an inactive derivative (or less active derivative) of the active component described herein. While, inactivity or reduced activity or reduced efficacy (e.g., less potency) may be desired in some instances, it may also be undesirable in other instances.

The active compositions described herein may comprise any amount up to about 50 wt. % of the active component in a solution comprising the solvent (water or organic compound). In some embodiments, the active component is one or more of an ethylated and/or methylated fatty acid or fatty acid ester in the solution comprising the solvent (water or organic compound). The combination of the active component and the solvent may be provided in solution as a dispersion. In some embodiments, the amount of the active component(s) in said dispersion may be greater than 50 wt. %. Solubility or dispersibility may be reduced when the amount of the active component is greater than 50%. In some embodiments, the amount of the active component (e.g., ethylated and/or methylated fatty acid or fatty acid ester) in said dispersion may be less or much less than 50 wt. %. For example, the dispersion may be provided as about a 50% solution (dispersion having 50% active component), or as about a 40% solution (dispersion having about 40% active component), or as about a 30% solution (dispersion having about 30% active component), or as about a 20% solution (dispersion having about 20% active component), or as about a 15% solution (dispersion having about 15% active component), or as about or up to about a 10% solution (dispersion having about or up to about 10% active component), or as about or up to about a 9% solution (dispersion having about or up to about 9% active component), or as about or up to about a 8% solution (dispersion having about or up to about 8% active component), or as about or up to about a 7% solution (dispersion having about or up to about 7% active component), or as about or up to about a 6% solution (dispersion having about or up to about 6% active component), or as about or up to about a 5% solution (dispersion having about or up to about 5% active component), or as about or up to about a 4% solution (dispersion having about or up to about 4% active component), or as about or up to about a 3% solution (dispersion having about or up to about 3% active component), or as about or up to about a 2% solution (dispersion having about or up to about 2% active component), or as about or up to about a 1% solution (dispersion having about or up to about 1% active component), or as about or up to about a 0.5% solution (dispersion having about or up to about 0.5% active component), or as about or up to about a 0.1% solution (dispersion having about or up to about 0.1% active component), or as about or up to about a 0.05% solution (dispersion having about or up to about 0.05% active component), or as about or up to about a 0.01% solution (dispersion having about or up to about 0.01% active component), or as about or up to about a 0.005% solution (dispersion having about or up to about 0.005% active component), or as about or up to about a 0.001% solution (dispersion having about or up to about 0.001% active component), and any range or combination of ranges therein. Unexpectedly, the dispersion may be as low as about a 2% solution (dispersion having as low as about 2% active component), or as low as about a 1% solution (dispersion having be as low as about 1% active component), or as low as about a 0.5% solution (dispersion having about or as low as about 0.5% active component), or as low as about a 0.1% solution (dispersion having as low as about 0.1% active component), or as low as about a 0.05% solution (dispersion having as low as about 0.05% active component), or as low as about a 0.01% solution (dispersion having as low as about 0.01% active component), or as low as about a 0.005% solution (dispersion having as low as about 0.005% active component), or as low as about a 0.001% solution (dispersion having as low as about 0.001% active component), and any range or combination of ranges therein. Said dispersion may be further lyophilized, crystallized or otherwise provided in a powder form.

In use, the composition (having at least the active component and the solvent and/or organic compound) is typically active against certain Gram positive bacteria. As further described below, the composition or its active component(s) may be provided at much lower concentrations to be as effective as comparative compositions, which must be provided at higher concentrations. In some embodiments, concentrations of the composition or its active component for internal use and/or topical application may be up to about 5 wt. % as a final concentration, or up to about 2.5 wt. % as a final concentration, or up to about 1 wt. % as a final concentration, or less than about 5 wt. % as a final concentration, or may be at or about or up to about 3 wt. % as a final concentration, or may be at or about or up to about 2 wt. % as a final concentration, or may be at or about or as low as about 1.5 wt. % as a final concentration, or may be at or about or as low as about 1 wt. % as a final concentration, or may be at or about or as low as about 0.5 wt. % as a final concentration, or may be at or about or as low as about 0.1 wt. % as a final concentration, or may be at or about or as low as about 0.05 wt. % as a final concentration, or may be at or about or as low as about 0.01 wt. % as a final concentration, or may be in any range or any amount therebetween. In a final concentration, the active component may be between about 0.001 wt. % and up to about 10 wt. % as a final concentration, or may between about 0.001 wt. % and up to about 5 wt. %, or may be between about 0.001 wt. % and up to about 1 wt. %, or may be between about 0.001 wt. % and up to about 0.5 wt. %, or may be in any amount or in any range therebetween. Higher concentrations of the composition or the active component(s) are possible, such as up to about 50% wt./vol., but are typically provided as concentrates and not generally utilized internally or topically. Compositions described herein may be provided in amounts in accordance with the MIC value for one or more of the target microorganisms. Concentrations below the MIC may still be provided and will exhibit activity but is reduced.

Both a concentrated composition and one or more dilute compositions are described herein. All of which are suitable for storage, including long term storage, including storage at ambient or room temperature.

In some embodiments, compositions as described herein for internal use and/or for topical application further comprise at least about 0.001 to about 20 wt. % of a phospholipid (i.e., double chained lipid with phosphate head group). In some embodiments, such as for internal and/or topical use, the composition may further comprise at least about 0.001 wt. % and up to about 10 wt. % of the phospholipid, or between about 0.001 wt. % and up to about 5 wt. % of the phospholipid, or between about 0.001 wt. % and up to about 1 wt. % of the phospholipid, or the phospholipid may be in any amount or in any range therebetween. In some embodiments, the phospholipid is a neutral phospholipid. In some embodiments, the phospholipid may be charged, such as for coating. In some formulations, the phospholipid is from an animal source. In some formulations, the phospholipid is from a vegetable source. The phospholipid may be lecithin. The lecithin may include a lipid material with a choline and inositol, the lipid being a fatty acid having a chain length from predominantly about C14 to C20. The phospholipid or lecithin may be phosphatidylcholine (PC). The phospholipid or lecithin may include a mixture of PC with any of the naturally occurring components of lecithin or by products, also considered lecithins, including but not limited to phosphatidylethanolamine (PE), phosphatidylinositol (PI), phosphatidic acid (PA), phosphatidylserine (PS), and lysophospholipids (LP) (e.g., lyso-phosphatidylethanolamine (LPE), sphyingomyelin (SPM)). The lecithin may be from a natural source, such as egg lecithin, soy lecithin, as examples. The lecithin may be enriched and/or further processed to enrich one or more of the lipid materials (e.g., the PC, PE, PI, PA, and/or LP). For the active compositions described herein, a large variety of lecithins from various sources were evaluated with similar findings. In some embodiments, the lecithin and/or the phospholipid is provided with an organic compound or in a solution comprising the organic compound. The organic compound may be the same organic compound used with or to disperse the active component (when dispersed by the organic compound). In some embodiments, the phospholipid when provided in the composition may be provided in a concentrated form or may be diluted before dispersing. The phospholipid as phosphatidylcholine and/or lecithin helps maintain the active component in suspension. The phospholipid as phosphatidylcholine and/or lecithin improves activity of the active component. The phospholipid and/or lecithin are suitable and biodegradable carriers for the active component. The phospholipid and/or lecithin may cause the active component to be provided as a pro-drug. Any phospholipid utilized as described herein may be in a form that is fully metabolized (e.g., not usually excreted by the kidneys).

When active compositions as described herein containing at least the described fatty acid(s) or fatty acid ester(s) and the phospholipid carrier, which may or may not be dispersed in the solvent and/or organic compound(s), the fatty acid ester(s) are now and unexpectedly found to be have an even larger anti-inflammatory activity, and to be even more active against various skin or surface or internal microorganisms, having even greater activity, greater inhibition of growth and increased killing, even at low concentrations (in which the amount of active component is at or less than 5% wt/vol., or is at or less than 1% wt/vol., or is at or less than 0.5% wt/vol., or is at or less than 0.1% wt/vol., or is at or less than 0.05% wt/vol., or is at or less than 0.01% wt/vol.), including concentrations that are lower or significantly lower than the same fatty acid without the phospholipids as described herein. The phospholipid carrier is so prepared to form liposome and/or micelle nanoparticles, in which the double chained lipids with smaller head group areas (e.g., PE, PA+small charged metal, such as $Ca^{2+}$, and/or PS+small charged metal, such as $Ca^{2+}$) along with the active component described herein (e.g., fatty acid, fatty acid ester, fatty acid methyl ester, fatty acid ethyl ester) with or without the LPs (e.g., LPC, LPE), should assist in formation of a liposomal or micellar arrangement, even when combined with the double chained lipids having larger head group areas (e.g., PC, PG, PI, PA, SPM). The liposome or micelle nanoparticles are selected as having an average cross-sectional diameter at least in the nanometer range. Nanoparticles are suitable to internalize. Nanoparticles may be less than about 500 nm, or less than about 400 nm, or less than about 300 nm, or less than about 200 nm, or less than about 100 nm, or in any range therebetween. The phospholipid carrier may also be prepared to form liposome and/or micelle microparticles. The liposome or micelle nanoparticles may also be selected as having an average cross-sectional diameter at least in the micrometer range. Microparticles may be suitable for topical application on a surface or on skin.

In one embodiment, when the active component (e.g., fatty acid, fatty acid methyl ester, and/or fatty acid ethyl ester, as examples) is provided with the phospholipid in suspension, in which the phospholipid with the active components are caused to form liposome and/or micelle particulates, the surprising activity described herein is unexpected, with much lower dosing, more activity, greater inhibition of growth, greater killing, higher efficacy against non-beneficial microorganisms, and/or larger anti-inflammatory activity, as compared with that found without the neutral phospholipid. Thus, in one or more embodiments, the active compositions comprising the active component described herein will further include the carrier (e.g., the phospholipid, such as the lecithin, PC, and/or additional lecithin or lipid components) and caused to form particulates. The potency of the active component, especially as particulates, as described herein is significant. In some embodiments, the phospholipid is lecithin, providing the same or better benefits.

When the active component is combined as described above, it may, when initially combined, contain a solvent (water or organic compound). When water is present in the active composition or in a final formulation, the concentration of water may be up to about 30% or up to about 50% water (e.g., for emulsions or gels), or up to about 60% water, or up to about 65% water, or up to about 70% water, or up to about 75% water, or up to about 80% water, or up to about 85% water, or up to about 90% water, or up to about 95% water, or up to about 98% water or may be greater than about 90% water or greater than about 95% water. Similarly, the active component in a solvent solution or organic compound solution as described above may have up to about 30%, or up to about 50% solvent solution or organic compound solution (e.g., for emulsions or gels), or up to about 60% solvent solution or organic compound solution, or up to about 65% solvent solution or organic compound solution, or up to about 70% solvent solution or organic compound solution, or up to about 75% solvent solution or organic compound solution, or up to about 80% solvent solution or organic compound solution, or up to about 85% solvent solution or organic compound solution, or up to about 90% solvent solution or organic compound solution, or up to 95% solvent solution or organic compound solution, or up to about 98% solvent solution or organic compound solution, or may be greater than about 90% solvent solution or organic compound solution or greater than about 95% solvent solution or organic compound solution.

While others have shown that adding a phospholipid to other types of active ingredients may improve solubility of said other type of active ingredient, said findings have not previously shown that a phospholipid or a neutral phospholipid will convert a previously considered inactive component or poorly active component (e.g., the medium chain fatty acid described herein, such as the C-12 medium chain fatty acid, the ethyl ester medium chain fatty acid, the methyl ester medium chain fatty acid, the ethyl dodecanoate and/or the methyl dodecanoate) into an active component. Said findings have also not shown that such an addition (of the phospholipid) will significantly improve potency of a relatively inactive or poorly active component into the active agent as is now disclosed. The findings reported herein are also unexpected because lauric acid, for example, has been shown by others to exhibit low or reduced antibacterial activity when combined with a neutral phospholipid or phosphatidylcholine. Furthermore, lauric acid has been reported by others to have only a nonspecific and weak activity against both Gram negative as well as Gram positive bacteria when some activity has been reported. And laurate has been reported by others to stimulate inflammation.

In some embodiments, the active compositions described herein are found to exhibit selective activity against Gram positive bacteria with very little activity, no activity or only negligible activity against Gram negative bacteria.

In some embodiments, the active compositions described herein are found to exhibit selective activity against certain Gram positive bacteria while not targeting certain beneficial bacteria.

The active compositions described herein may further include, in addition to the phospholipid described above, another lipid in the form of a double chained phospholipid and/or cholesterol (a bulky lipid, rather than a single chain or free fatty acid lipid). This additional lipid when included may be in any amount in the range of total amounts between about 0.001 wt. % and 6 wt. % based on the total weight of the composition. This additional lipid may be in a smaller amount, to assist in emulsion stability and/or micellar or liposomal formation. This lipid is may be included to prevent aggregation, flocculation, coalescence, and/or creaming of the micelles or liposomes when formed. Still further modifications or carrier features may be made to the described compositions to target said composition to one or more specific tissues. The particulated liposomes or micelles may be coated to target delivery. The particulated liposomes or micelles may be coated to delay delivery. The coating may comprise any, some or all of linear polysaccharides, antibodies, functionalized polymers, and/or proteins, such as albumin.

In some embodiments, the active composition described herein is provided as or includes nanoparticulates comprising the active component and lecithin in the amounts previously described.

In some embodiments, the active composition described herein is provided as or includes nanoparticulates comprising at least the active component and lecithin, with or without cholesterol or other lipid, in the amounts previously described.

In some embodiments, the active composition is provided as or includes nanoparticulates comprising at least the active component, a phosphatidylcholine, with or without cholesterol or other lipid, in the amounts previously described.

In some embodiments, the active composition is provided as or includes nanoparticulates comprising at least the active component, a phosphatidylcholine, with or without cholesterol or other lipid, and bile or bile salts or bile acids, in the amounts previously described.

Many or most of the components in the compositions described herein are not soluble in water, although the solvent for the active component may be an aqueous solvent. The described compositions, however, do not require an additional surfactant or detergent for said activity, such as sodium laurel sulfate or other sulfates or sulfonates or ethoxylates or glucosides or succinates or alkanolamides or amine oxides, as examples, as is typically included by others when one or more fatty acids are added to a composition, such as for topical disinfectant use. The described compositions do not require an additional antimicrobial for said activity, such as a quaternary ammonium compound or an ether or halogenated ether or amino acid or chlorhexidine, as examples, as is typically included by others when one or more fatty acids are added to a composition, such as for topical disinfectant use. In one or more embodiments, the phospholipid(s) and lecithins in the compositions described herein are metabolized, hence biodegradable. The described active compositions do not require an additional emulsifier, flow agent or stabilizer for activity, as is typically included by others when one or more fatty acids are added to a composition, such as for topical disinfectant use.

In some embodiments, when properly dispersed and suspended, the active formulation described herein, upon combining or suspending the active component (e.g., the described fatty acid, fatty acid ester, ethyl or methyl fatty acid ester with or without the phospholipid and/or the other lipid) with the solvent solution or the organic compound solution, forms an optically clear suspension. The suspension may be utilized. The suspension may be dried prior to use. In addition or as an alternative, the composition as a suspension or in dry form may be a concentrate that is diluted at the time of use or some time prior to use.

In a representative method, the active composition described herein is prepared with the active component, for example, any of the described fatty acids (alone or in combination), an example of which is an esterified ethyl or esterified methyl saturated fatty acid with 12 carbon atoms or with between 12 and up to 18 carbon atoms, and at least the solvent or organic compound, the organic compound being an organic compound in solution. The combination may have as much as 50% (by weight) of the active component and as little as 0.001% (by weight) or even less of the active component. The active component may be initially combined with or suspended in the solvent or in water, and to this suspension, the organic compound (often in solution) is combined. The solvent or organic compound in solution may also be prepared and to this is combined the active component. The organic compound may be an alcohol or may be chloroform, as examples. The combination of the active component and the at least the organic compound is caused to suspend in a suspension by combining vigorously or by agitation or shaking. The vigorous combining or mixing may be by sonication. The combining or mixing may include heat. Heating may be above room temperature or may be at ambient temperature. Heating may be at or about 37 degrees Centigrade and is typically not greater than about 50 degrees, or 55 degrees, or 60 degrees Centigrade. In one or more embodiments, the suspension may be caused to form particulates by addition in the amounts previously described of a phospholipid, such as phosphatidylcholine and/or a lipid in a smaller amount (e.g., cholesterol or lecithin) followed by mixing as described above. The phospholipid or phosphatidylcholine and/or a lipid may be initially provided to an organic compound in solution prior to combining with the suspension. The active component in the solvent or organic compound solution may also be combined and suspended with the phospholipid or phosphatidylcholine and/or a lipid in the same or compatible solvent or organic compound solution. The organic compound solution may include a buffer to maintain stability and/or pH of the suspension. The suspension may be used as is. The suspension may be further diluted (e.g., when prepared as a concentrate). This composition may be further processed into a suitable or desired form for an internal and/or topical formulation for internal and/or topical application, respectively.

In some embodiments, after the mixing to cause the suspension, some or all of the organic compound may be evaporated off. Evaporation may be performed by known methods of evaporating an organic compound. For example, evaporation may include placing the composition in a freeze dryer under vacuum. In some embodiments, it may be preferable to evaporate without heat. Other suitable or known means of evaporations may be used. The evaporated composition may be utilized or may be further processed into a suitable or desired form for an internal and/or topical formulation for internal and/or topical application, respectively. Further processing may include filtering, lyophilizing, coating, as examples. Interestingly, the active component in the composition may not be simply in a form of a saturated fatty acid (acidic form). This is because when preparing simply a saturated fatty acid that is an acid, such as a medium chain fatty acid or lauric acid (i.e., in its acid form), with the organic compound to cause a suspension, it has been found that the lauric acid could precipitate out of the suspension. In some embodiments, a small fraction of the lauric acid may remain suspended and be available for use or for combining with the neutral phospholipid or phosphatidylcholine and/or lecithin with or without the further lipid. In some embodiments, an esterified form of the fatty acid is preferred. It has been found that by preparing a composition with the described fatty acid in an esterified form, such as a laurate, more or most or substantially all of said fatty acid remains in the suspension without precipitating out, especially when preparing a composition in which the active component comprises less than 50% of the composition.

In other representative methods, the active composition described herein was prepared by initially combining said active component (for example, an esterified ethyl or methyl saturated fatty acid with 12 or greater carbon atoms) and a solvent. In one example, the active component is at least a lauric acid ethyl ester. In one example, the active component is at least a lauric acid methyl ester. The solvent may be water. The solvent may be an organic compound in solution. A representative initial mixture may be a dispersion. A representative initial mixture may have about or up to about 99.9% (by weight) solvent (water and/or organic compound) or between about 50% and about 99.9% solvent (water and/or organic compound) and as much as or up to about 50% (by weight) of the active component or as little as 0.001% and up to about 50%, or between about 0.001% and about 10% of the active component. Of course, any range or amount of active component and solvent previously disclosed may be used. To this suspension, a second suspension comprising a phospholipid is added. The second suspension may comprise lecithin and/or PC. In one example, the second suspension contained the lecithin and/or PC in an organic compound in solution. The lecithin and/or PC may, in some embodiment, be up to about 50% in a solution of the organic compound or up to about 10% in the solution of the organic compound or between about 0.001% and about 10% or between about 0.001% and about 5%. In one example, the lecithin and/or PC is not more than 50%, as solubility becomes an issue with amounts of about 50% lecithin and/or PC or amounts greater than about 50% lecithin and/or PC. In some examples, the lecithin and/or PC is about 8%, or is about 7%, or is about 6%, or is about 5%, or is about 4%, or is about 3%, or is about 2% in the second suspension. Of course, any range or amount of the lecithin and/or PC previously disclosed may be used. The organic compound could be the same organic compound provided with the active component. In one example, the organic compound for the second solution is a weak acid (e.g., acetic acid). In one example, the organic compound as a weak acid was buffered with a suitable buffer (e.g., sodium acetate) for stability of the organic compound in the solution. The first suspension and the second suspension are combined and mixed vigorously or agitated or shaken. In one example, the first suspension containing about 10% active component is combined with about 90% of the second suspension, such that when combined, the combination includes less than about 10% lecithin and/or PC, and less than about 5% active component, in the organic compound (e.g., the weak acid or the buffered weak acid). In one example, the mixing is by sonication. Other means of vigorous mixing are readily contemplated, as understood by one of ordinary skill in this field. The mixing causes a particulated suspension comprising liposomes or micelles. In some embodiments, sonication as the form of mixing has been found to improve activity of the active composition. In some embodiments, smaller liposomes may be preferred, as these are found to increase activity of the composition (e.g., about or less than about 300 nm or about or less than about 200 nm). Smaller nanoparticles may be caused by high pressure filtration or other methods known to one of ordinary skill in the relevant field. The mixing may or may not include heat. Heating may be above room temperature or may be ambient temperature. Heating may be at or about 37 degrees Centigrade and is typically not greater than about 40 or 50 or 60 degrees Centigrade. The particulated suspension comprising the active component and the lecithin and/or PC may further comprise a lipid, such as cholesterol or additional lecithin component, in the amounts previously described. The suspension may comprise simply the active component and lecithin. The suspension may be used as is, or may be diluted in a formulation for topical and/or internal use. In some embodiments, the active composition may undergo further processing, such as a filtering step, lyophilizing, coating, as examples. It has been found that high pressure filtering improves activity of the particulated active composition.

In any of the methods described above, the active compositions may be further processed so as to provide the active composition in a lyophilized or granulated or powder form.

In any of the methods described above, the composition may undergo a coating step. The coating may be provided after mixing the composition and causing the particulated suspension or emulsion (comprising the liposomes or micelles). The coating may occur before or after filtering. The coating may occur before or after evaporation. The coating may occur before or after drying and/or lyophilizing. In one or more embodiments, the coating step is found to improve stability of the compositions. In one or more embodiments, the coating step is found to improve activity of the compositions. The coating may include spray coating, dipping, chemical bonding or otherwise adhering one or more coatings on the liposomes or micelles. In some embodiments, the coating includes linear polysaccharides. Examples of the linear polysaccharide include, but are not limited to, oligosaccharides, starches, glycogen (including glycols), cellulose, algin (alginate), chitin, pectin, and combinations thereof. In some embodiments, a more water-soluble derivative is included, such as chitosan. The coating step provides or involves an adhesion of the linear polysaccharide with the liposomes or micelles. The coating step may include adding to the liposomes or micelles or the particulated suspension at least one of the linear polysaccharides. The linear polysaccharide may be preselected for higher interaction with a certain cell or cell type. The linear polysaccharide may be acidic, anionic, or modified with one or more carboxyl groups, phosphate groups, sulfur esters, or ester groups to selectively interact when introduced internally or topically. The coating step typically includes a chemical interaction between the surface of the liposome or micelle and the linear polysaccharide. Adhesion may be promoted by a charge modification made to one or more of the liposome or micelle and the linear polysaccharide. Adhesion may be promoted by functionalizing the coating or the liposome or micelle. In one example, adhesion of the linear polysaccharide with the liposomes or micelles may include a blending step. The blending may comprise stirring the particulates or the particulate suspension with the coating material, such as the linear polysaccharides. The coating material may be provided in any amount. The coating material may be soluble in the suspension. In one example, up to 50% w/v or up to 20% w/v, or up to 10% w/v with the particulates or the particulated suspension is combined with a solution comprising the coating material, such as linear polysaccharides, an example of which is chitosan. The coating solution may be any amount. The coating solution may be 1.5%, or may be less, or may be greater. Of course, any concentration may be provided. The coating material, such as chitosan, may be in the same organic compound solution as the liposomes. In one example, adhesion of the coating material on the particulates or particulated suspension may include spraying or blending, which may, in some embodiments, be followed by an incubation step. The incubation may include incubating for a few minutes, or one hour or for several hours or overnight. The coating step may include a suspension/dispersion and/or drying phase. Alternative methods for adhering the one or more coating materials are known in the relevant art and are contemplated. Several coating steps may be performed in series, with the same or different coating materials. After coating, the active coated particulated compositions may be agitated, such as by sonication, to ensure particulation and causing of liposomes or micelles. In some embodiments, the coated particulated compositions undergo filtering, such as a high pressure filtering, as this has been found to improve activity of the coated particulated composition.

The coating step when included provides additional protection for the particulated liposomes or micelles, enhancing stability, and/or life span when provided in a formulation for use internally and/or topically. In one or more embodiments, the coating step improves the activity (inhibitory or killing effect or anti-inflammatory effect) of the active coated particulated composition when provided in a formulation for use internally and/or topically. In one or more embodiments, the coating step improves the activity (inhibitory or killing effect or anti-inflammatory effect) of the active particulated composition by at least or by about 10%. In one or more embodiments, the coating step improves the activity (inhibitory or killing effect or anti-inflammatory effect) of the composition by at least or by about 50%. In one or more embodiments, the coating step improves the activity (inhibitory or killing effect or anti-inflammatory effect) of the composition by at least or about 100%. In one or more embodiments, the coating step improves the activity (inhibitory or killing effect) of the composition by at least or by about 500%. In one or more embodiments, the coating step improves the activity (inhibitory or killing effect or anti-inflammatory effect) of the composition by at least or by about 1000%.

For internal use, in addition to or as an alternative to coating, the described composition may be provided with or without bile or provided in a solution of one or more bile salts and/or bile acids. When added with the bile or the solution of the one or more bile salts/bile acids, the bile or solution of the bile salt/bile acids may be included after evaporation of the organic compound and/or after high pressure filtering. The bile or solution of bile salts/acids may be added in a quantity of at or about 2%, or about 1%, or about 0.5%, or may be less than about 2% by weight. Other lower amounts may also be used.

In some embodiments or preferably, the described active composition is used as a replacement for an antibiotic treatment against a Gram positive bacteria, because newer antibiotics are now proving to be ineffective or less effective within as short a period of time as 18 months after introduction into the population, as resistant bacterial strains are developing within as short as 18 months after introduction of the antibiotic.

The described active compositions are not believed to promote drug resistance because, without being bound by theory, the described compositions are believed to act directly on the physical composition of the bacterial membrane.

The described compositions are found to be effective against non-beneficial Gram positive bacteria, such as but not limited to *Staphylococcus* spp., *Streptococcus* spp., *Clostridium* spp. The described compositions are found to be effective against *Candida* spp.

For internal use, the described composition may be provided orally, generally either once, or in divided doses. The described composition may be provided as a wash, such as for the mouth or body. Similarly, the described compositions may be provided as is, or in an emollient, or in an evaporating solution, or in a lotion or cream and applied topically. The described composition may also be provided as an inhalant, parenterally, intramuscularly, or by IV. Excipients suitable for administration may be included. Often, minimal or few excipients are included.

In some embodiments, the active component was provided as a methyl laurate or as an ethyl laurate in a composition that included a phospholipid, such as PC or lecithin and/or cholesterol. The methyl laurate or ethyl laurate are esterified fatty acids having a chain length of 12 carbon atoms. These active components were provided in active compositions that included a phospholipid, such as PC or lecithin and/or cholesterol. Said compositions were tested against a variety of bacteria using amounts of the active component ranging from 0.0009 wt. % to 8 wt. %. The bacteria included *Escherichia coli, Clostridium difficile, Streptococcus pyogenes, Streptococcus mitis, Streptococcus mutans, Staphylococcus aureus* (and MRSA strains), *Staphylococcus epidermidis, Lactobacillus*, and *Bifidobacterium*. The minimum inhibitory concentration (MIC) of the active component (e.g., the ethyl laurate or the methyl laurate) needed to prevent growth of the target bacteria was evaluated based on a method published by Clinical Laboratory Standards Institute (CLSI), broth microdilution method M-07 (M07). MIC of fungi was evaluated in accordance with a method published by CLSI, broth microdilution method M-27 (M27). Representative MIC values are depicted in TABLES 1, 2 and 3. TABLE 1 shows some representative MIC data obtained, using either ethyl laurate (EL) or methyl laurate (ML) as the active component in compositions prepared as described with a first example, in which the amount of the active component was in a range between 0.08 wt. % and 5 wt. %. In Table 1, >>5% indicated no inhibitory effect. In Table 2 the amount of the active component was in a range of between 0.08 mg/ml and 8 mg/ml. In Table 2, >8 indicated no inhibitory effect. In Table 3 the amount of the active component was in a range of between 0.0009 µg/ml and 8 µg/ml. In Table 3, >>5% indicated no inhibitory effect.

TABLE 1

| organism | active component | MIC |
| --- | --- | --- |
| E coli | EL | >>5% |
|  | ML | >>5% |

TABLE 1-continued

| organism | active component | MIC |
| --- | --- | --- |
| C. difficile | EL | 0.5% |
|  | ML | 1% |
| S. pyogenes | EI | 0.5% |
|  | ML | 0.5% |
| S. mitis | EL | 0.5% |
|  | ML | 0.5% |
| S. mutans | EL | 0.5% |
|  | ML | 0.5% |
| S. aureus | EL | 0.5% |
|  | ML | 0.5% |
| S. epidermidis | EL | 0.5% |
|  | ML | 0.5% |
| Lactobacillus spp. | EL | >>5% |
|  | ML | >>5% |
| Bifidobacterium | EL | >>5% |
|  | ML | >>5% |
| Candida | EL | 0.5% |
|  | ML | 0.5% |
| Mycobacterium | ML | 0.5% |
|  | EL | 1% |

TABLE 2

| organism | active component | MIC (mg/mL) |
| --- | --- | --- |
| E coli | EL | >8 |
|  | ML | >8 |
| C. difficile | EL | 0.8 |
|  | ML | 0.8 |
| S. mutans | EL | 0.8 |
|  | ML | 0.8 |
| S. aureus | EL | 0.8 |
|  | ML | 0.8 |
| L. acidophilus | EL | >8 |
|  | ML | >8 |
| B. bifidum | EL | >8 |
|  | ML | >8 |
| C. albicans | EL | <0.08 |
|  | ML | <0.08 |
| M. bovis | ML | 2 |
|  | EL | 2 |

TABLE 3

| organism | active component | MIC |
| --- | --- | --- |
| E coli | EL | >>5% |
|  | ML | >>5% |
| C. difficile | EL | 0.0018% |
|  | ML | 0.0018% |
| S. pyogenes | EI | 0.0018% |
|  | ML | 0.0018% |
| S. mitis | EL | 0.0018% |
|  | ML | 0.0018% |
| S. mutans | EL | 0.0018% |
|  | ML | 0.0018% |
| S. aureus | EL | 0.0018% |
|  | ML | 0.0018% |
| S. epidermidis | EL | 0.0018% |
|  | ML | 0.0018% |
| Lactobacillus spp. | EL | >>5% |
|  | ML | >>5% |
| Bifidobacterium | EL | >>5% |
|  | ML | >>5% |
| Candida | EL | 0.0018% |
|  | ML | 0.0018% |
| M. bovis | ML | 0.0018% |
|  | EL | 0.0018% |

In a first example, 1 wt. % methyl laurate or ethyl laurate was combined with 9 ml of water and 1 ml of chloroform. The mixtures were agitated vigorously to form suspensions, followed by removal of the chloroform under vacuum using a freeze dryer. After removal of the chloroform, the suspensions were optically clear. In these examples, the optically clear suspensions were combined with 2% bile when evaluating activity against various bacteria. It was found that suspensions containing the ethyl laurate were completely bacteriostatic against strains of *Staphylococcus*. The suspensions containing methyl laurate significantly retarded bacterial growth. (See, Tables 1 and 2).

The compositions of the first example were also evaluated for effects on T-cell proliferation in blood cell model. Briefly, T cells were stimulated for 24 h. All were given killed bacteria at 1000 per ml, T cells were 1000000 per ml. Control was given water, as compared with compositions of the first example or cyclosporine, a known anti-inflammatory agent. The concentration of the first sample was a final concentration of 0.5% of the active component. T cell proliferation was given as the number of T cells present per ml at 24 hours. The compositions containing methyl laurate or ethyl laurate at 0.5% were found to be as effective as a known or comparative anti-inflammatory agent, cyclosporine, in preventing T cell proliferation in response to stimulation by *Staphylococcus aureus* in an in vitro model of blood T cell stimulation. Compositions containing ethyl laurate were also found to provide a larger anti-inflammatory effect on T-cell proliferation as compared with cyclosporine. FIG. 1 depicts a representative example with the ethyl laurate (EL), in which data above the dashed line indicates increased T cells. These compositions of the first example also inhibited growth of skin bacteria (*Staphylococcus* spp.), an effect that was not found with cyclosporine. (Tables 1 and 2). Effects provided by the active component in lecithin particulates will be as effective if not much more effective, given their higher potency and activity as an antimicrobial.

In a second example, a first suspension was made with 2.2% lecithin in a solution of 98 mM acetic acid and 2 mM sodium acetate. A second suspension comprising about 10% active component (at least methyl laurate or ethyl laurate in solvent) was prepared. The first and second suspensions were combined, in which 90% of the combination was the first suspension and 10% of the combination was the second suspension. This provided a combination which contained about 2% lecithin, and about 1% of the active component. This was sonicated and then filtered by higher pressure filtration and formed particulated liposomes containing the active component that when tested were even more active against strains of *Staphylococcus, Streptococcus* and *Clostridium difficile* (e.g., MIC of the active component was 16 mg/ml or a concentration of 1.6%, obtained using the CLSI broth microdilution methods described previously). The composition was not active against *E. coli* (a Gram negative bacteria) and was not very active against beneficial gastrointestinal microorganisms, such as *Lactobacillus* spp. and *Bifidobacterium*.

In a third example, the liposomal composition of the second example was coated by mixing with amounts of chitosan, in which the chitosan was added to the composition in several amounts up to about 10% (w/v). Chitosan was provided in solution (e.g., in the same buffer or organic compound for causing the liposomes). The mixing included stirring. This was followed by sonication and then high pressure filtration. The filtered composition (coated liposomes containing the active component) when tested was found active against strains of *Staphylococcus, Streptococcus* and *Clostridium difficile*. For example, with a 1.5% solution of chitosan (in a solution comprising the organic compound solution used with the second example) combined with the liposome compositions of the second example (liposomes containing lecithin and active component), a coated liposomal composition was prepared comprising about 0.75% chitosan, about 1% lecithin and about 0.5% of the active component. MIC of the active agent comprising the chitosan nanoparticulate formulation was 18 µg/ml, a concentration of 0.0018%, obtained using the CLSI broth microdilution assay described above. This composition was significantly less active against *E. coli* (a Gram negative bacteria) and, similarly ineffective against beneficial gastrointestinal microorganisms, such as *Lactobacillus* spp. and *Bifidobacterium*. The MIC was >8 mg/ml. Activity was seen against Gram positive, but not Gram negative bacteria. Non-target organisms *Lactobacillus, Bifidobacterium, E. coli* had an MIC>8 mg/ml.

The above findings showed improved activity of compositions described herein having the phospholipid in addition to the active component, which when caused to form liposomes or micelles, displayed the selective activity against certain, less beneficial Gram positive bacteria. Coating of the liposomal and/or micellar compositions described herein further improved activity of the compositions described herein. MICs were also lower when the formulations achieved better temperature stability. Accordingly, the MICs will be lower for said compositions described herein against at least *C. difficile, S. pyogenes, S. mitis, S. mutans, S. aureus, S. epidemidis,* and *Candida*.

The compositional formulations may be provided in the form of a liquid, suspension, tablet, caplet, capsule, granules, lozenges, mouthwash, cream, lotion, and the like. Many of the formulations may include one or more of a film coating composition, excipients, and optionally a colorant and/or flavorant. The composition may be further formulated for immediate release or delayed release, e.g., fast-release, or controlled, sustained, or delayed-release. The excipient may and should be a compendial (USP/NF/Ph.Eur.) grade. Any colorants should be certified by its supplier to meet the current Color Additive Regulations for at least the US and/or the EU. Said compositions may be manufactured for increased oral bioavailability or topical bioavailability, having an increased dissolution rate of the active components, thereby providing improved efficacy. Some of the compositions may be manufactured by one or more of layering, hot-melt extrusion, and/or lipid delivery, as examples. Manufacturing of the formulations for administration as described herein may also include non-aqueous granulating, de-lumping, drying, milling, lubricating and/or tableting, capsuling, optionally followed by film coating. Formulations, including tablets, caplets, capsules, granules and the like will exhibit satisfactory chemical and physical stability, dissolution profiles, and should have batch-to-batch consistency. Manufacturing may also include dry granulation (e.g., roller compaction or direct compression; mixing, followed by compression). In some embodiments, a dry granulation form is likely to provide enhanced stability outcome. When packaged, the packaging may include an induction-sealed opaque high density polyethylene bottle with plastic cap or glass bottle, or other suitable container, or may be individually packaged or wrapped. Any packaged compositions should maintain their physical and chemical stability, such as for up to 2 years, when stored at or about 25° C. (at or about 77° F.), with variations ranging from about 15°–30° C. (about 59°–86° F.). Hard gelatin or soft gelatin capsules are also contemplated, using known methods. Various composition strengths may be provided.

Formulations of the described composition can be administered for internal and/or external activity at or around the MIC for inhibiting of growth and/or killing of the select Gram positive bacteria or yeast. Higher and lower doses can also be administered with greater or lesser efficacy. Formulations of the described composition can be administered for internal and/or external activity at or around the MIC for anti-inflammatory activity. Formulations of the described compositions can also be administered outside the MIC and still provide anti-inflammatory activity.

For safety, efficacy, and pharmacokinetics (PK) of the described composition, one or more of the following can be evaluated, as representative examples: the treatment or improvement of skin and skin structure infections (SSSI), of acute bacterial skin and skin structure infections (ABSSSI), and genito-urinary tract infections. ABSSSI may be caused by streptococci and/or staphylococci, including MRSA. By prolonging the time at or near the Cmax, exposure to the compositions described herein will increase, resulting in an increase in efficacy.

The described composition may be provided as a selective antibacterial agent against certain, non-beneficial or less beneficial Gram positive bacteria. The described composition, as a selective agent may also be combined with another treatment, such as a probiotic, to encourage growth of Gram negative bacteria, such as in the gastro-intestinal tract where several types of Gram negative bacteria are considered beneficial. Thus, in one or more embodiments the described composition is provided in combination with a probiotic.

Efficacy and alternative dosing of any of the compositions described herein may be determined by pharmacokinetic and/or pharmacodynamics analysis against drug-resistant and clinical strains of at least *Streptococcus* spp., *Staphylococcus* spp., *Mycobacterium* spp., *Clostridium* spp., and *Candida*, as examples. MIC range, $MIC_{50}$, $MIC_{90}$, FIC, and MIC distributions will determine alternative amounts for internal and/or topical use.

The described compositions are found to be effective against bacteria, such as but not limited to *Streptococcus* spp. (including but not limited to *Streptococcus pneumoniae, Streptococcus pyogenes, Staphylococcus* spp. (including but not limited to resistant *Staphylococcus aureus* (MRSA, VRSA), *Mycobacterium* spp. (including but not limited to *M. bovis*). The described compositions should also be active against bacterial strains of the clinically significant species that are resistant to quinolones, doxycycline, macrolides, clindamycin, cotrimoxazole, beta-lactams, and other classes. The compositions described herein are believed to affect the outer lipid membrane, will make it possible for the described compositions to enter the cell and/or otherwise promote their killing effect on the microorganism. Thus, as described herein, any mutation or alteration of the bacterial membrane sufficient to confer resistance to the active agent described herein will likely render the bacteria non-viable. Thus, it is expected that the occurrence of resistance conferred by spontaneous mutational bacteria or fungi when in the presence of any of the described composition will be markedly lower than what is found in antibiotics currently available for prevention or treatment of infections associated with the vulnerable or susceptible microorganisms described herein.

The described compositions are found to be effective as an anti-inflammatory, particularly in response to a trigger by the microorganisms described above. The described compositions should also be especially effective when inflammation or inflammatory activity is stimulated by bacterial strains of the clinically significant species that are susceptible or resistant to other classes of antibiotics. The compositions described herein are therefore found to exhibit a dual effect in response to infection from a bacteria or fungi, making it of greater benefit as compared with many other classes of antibiotics. It is expected that the reduction in inflammatory activity, and at least the benefits associated with the reduction in T-cell proliferation, provided by any of the described compositions, will be observed as long as the described composition is available to illicit such a response (or until cell killing is achieved). This anti-inflammatory behavior is significant and appears to be both a novel and effective outcome associated with the active compositions described herein, even when concentrations of the active composition are outside of the MIC of the vulnerable or susceptible microorganisms described herein.

The described compositions will overcome and address at least one of the following: poor oral absorption; profound food effects; site-specific absorption; sensitivities, particle size, process variables, polymorphic forms, salt forms or hydration state; common ion effect. The described compositions will provide a synergistic effect in the combinations described (e.g., combinations with organic compound, lecithin, PC, other lipids, coating, and/or probiotic, etc.). The described compositions provide enhanced target access of a normally poorly penetrating and poorly active or inactive medium chain (C-12) or long chain (C-13 to C-18) fatty acid when provided internally and/or topically (without the combinations described herein). The described compositions have primary activity against Gram-positive pathogens with little or no activity against Gram-negative species. The described compositions provide increased survivability internally. The described compositions provide excellent Gram-positive spectrum against non-beneficial microorganisms without Gram-negative activity, thereby offering an agent with synergistic potential and a better outcome.

Although representative processes and articles have been described in detail herein, those skilled in the art will recognize that various substitutions and modifications may be made without departing from the scope and spirit of what is described and defined by the appended claims.

What is claimed is:

1. A composition with microbial growth inhibitory activity, the composition comprising:
    an active component of esterified fatty acids, the esterified fatty acids being selected from one of ethyl dodecanoate and methyl dodecanoate, wherein the active component is in a total amount up to about 50 wt. % of the composition;
    an organic carboxylic acid as a solvent having a pH of between about pH 4 and pH 6; and
    phospholipids in an amount between about 0.5 and 50 wt. % of the composition, wherein the phospholipids are one of: (i) neutral phospholipids, and (ii) neutral phospholipids combined with at least one of a double chain phospholipid and cholesterol; and
    wherein the composition is in a suitable form for pharmacotherapy use as an antimicrobial, wherein the suitable form for pharmacotherapy use comprises at least one of a powder, particulate, gel, and suspension,
    wherein the composition is caused to form liposomes containing at least the phospholipids and the active component, and
    wherein the suitable form is active against and has growth inhibitory activity against pathogenic Gram-positive bacteria and yeast selected from at least one strain of at least one of *Staphylococcus* spp., *Streptococcus* spp., *Mycobacterium* spp., *Clostridium* spp. and *Candida* spp. without targeting beneficial natural Gram-positive bacteria selected from any one or more of *Lactobacillus*

*acidophilus* and *Bifidobacterium bifidum*, wherein at least one strain of at least one of the pathogenic Gram-positive bacteria and yeast is resistant to another and different class of antimicrobial.

2. The composition of claim 1, wherein the phospholipids are one or more of: phosphatidylcholine, phosphatidylethanolamine, phosphatidylinositol, phosphatidic acid, phosphatidylserine, lysophospholipid, and any combination thereof.

3. The composition of claim 1, wherein, excluding the active component, the composition comprises no additional free fatty acids having a carbon chain length from 6 to 12.

4. The composition of claim 1, wherein the esterified fatty acids are one or more of having a purity of about or greater than 90%, and having a pharmaceutical grade purity.

5. The composition of claim 1, wherein the composition further comprises at least one fatty acid having a carbon chain length from between 13 to 18.

6. The composition of claim 1, wherein the suitable form is any one or more of lyophilized, suitable for storing, and stable at ambient or room temperature.

7. The composition of claim 1, wherein the suitable form is for internal use by a subject in need thereof.

8. The composition of claim 1, wherein the suitable form is for topical use by a subject in need thereof.

9. The composition of claim 1, wherein the suitable form inhibits growth of at least two strains from a group consisting of *Staphylococcus* spp., *Streptococcus* spp., *Mycobacterium* spp., *Clostridium* spp. and *Candida* spp.

10. The composition of claim 1, wherein, when the active component is provided in an amount and at an MIC for growth inhibitory activity against at least one of the pathogenic Gram-positive bacteria and yeasts, or in an amount that is greater than the amount at the MIC for growth inhibitory activity against at least one of the pathogenic Gram-positive bacteria and yeasts, the suitable form is selectively active against at least one strain of at least one of a susceptible Gram-positive bacteria and yeast without targeting beneficial Gram-positive bacteria from one or more of oral mucosa, skin, and gastrointestinal tract.

11. A composition having microbial growth inhibitory activity, the composition comprising:
an active component of esterified fatty acids, the esterified fatty acids being selected from one of ethyl dodecanoate and methyl dodecanoate, the esterified fatty acids in an amount up to about 50 wt. % of the composition; and
phospholipids in an amount between about 0.001 and 50 wt. % of the composition, wherein the phospholipids are one of: (i) neutral phospholipids, and (ii) neutral phospholipids combined with at least one of a double chain phospholipid and cholesterol; and
wherein the composition is in a suitable form for pharmacotherapy use as an antimicrobial,
wherein the suitable form comprises at least liposomal nanoparticles comprising at least the active component and the phospholipids,
wherein the suitable form is active against and has growth inhibitory activity against pathogenic Gram-positive bacteria and yeast selected from at least one strain from at least one from a group consisting of *Staphylococcus* spp., *Streptococcus* spp., *Mycobacterium* spp., *Clostridium* spp. and *Candida* spp. without targeting beneficial natural Gram-positive bacteria selected from any one or more of *Lactobacillus acidophilus* and *Bifidobacterium bifidum*, wherein at least one strain of at least one of the pathogenic Gram-positive bacteria and yeast is resistant to another and different class of antimicrobial,
and wherein the composition is formed by at least the steps of:
combining the active component, an organic acid as a solvent, and the phospholipids, the organic acid having fewer than 3 linear carbons and a pH between about pH 4 and about pH 6; and
suspending and causing to form liposomes, wherein the liposomes contain at least the active component and the phospholipids.

12. The composition of claim 11, wherein the phospholipids are neutral phospholipids combined with at least cholesterol, and the cholesterol is in an amount between about 0.04 and 6 wt. % of the composition.

13. The composition of claim 11, wherein the phospholipids are one or more of: phosphatidylcholine, phosphatidylethanolamine, phosphatidylinositol, phosphatidic acid, phosphatidylserine, lysophospholipid, and any combination thereof.

14. The composition of claim 11, wherein the organic acid is any one of a weak short chain carboxylic acid, and a buffered weak short chain carboxylic acid.

15. The composition of claim 11, wherein the step of combining comprises at least one of: (i) combining the active component with the phospholipids and the organic acid; (ii) combining initially the phospholipids and the organic acid before adding the active component; (iii) combining the active component with the phospholipids and the organic acid, which is followed by at least a step of filtering; and (iv) combining initially the phospholipids and the organic acid before adding the active component, which is followed by at least a step of filtering.

16. The composition of claim 11, wherein the suitable form is for internal use by a subject in need thereof.

17. The composition of claim 11, wherein the suitable form is for topical use by a subject in need thereof.

18. The composition of claim 11, wherein the liposomal nanoparticles are lyophilized.

19. The composition of claim 11, wherein the liposomal nanoparticles are in a pharmaceutical formulation intended for internal administration to a subject in need thereof, for inhibiting growth of at least one strain of at least one of the pathogenic Gram-positive bacteria and yeast.

20. The composition of claim 11, wherein the liposomal nanoparticles are in a pharmaceutical formulation intended for topical administration to a subject in need thereof, for inhibiting growth of at least one strain of at least one of the pathogenic Gram-positive bacteria and yeast.

* * * * *